(12) United States Patent
An

(10) Patent No.: US 6,943,364 B2
(45) Date of Patent: Sep. 13, 2005

(54) MULTI-FUNCTIONED WAFER ALIGNER

(75) Inventor: Hyeon-Su An, Sungnam (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 212 days.

(21) Appl. No.: 10/084,284

(22) Filed: Feb. 26, 2002

(65) Prior Publication Data

US 2002/0125448 A1 Sep. 12, 2002

(51) Int. Cl.[7] .............................................. G01N 21/86
(52) U.S. Cl. ............................... 250/559.42; 356/237.4
(58) Field of Search ......................... 250/559.3, 559.36, 250/559.42–559.48; 356/400, 237.2, 237.4, 237.5; 414/935, 936

(56) References Cited

U.S. PATENT DOCUMENTS

| 4,819,167 A | * | 4/1989 | Cheng et al. ................. 700/59 |
| 4,880,348 A | * | 11/1989 | Baker et al. ................. 414/783 |
| 5,851,102 A | * | 12/1998 | Okawa et al. ............... 414/783 |
| 6,062,084 A | * | 5/2000 | Chang et al. ................. 73/601 |
| 6,298,280 B1 | * | 10/2001 | Bonora et al. .............. 700/218 |

FOREIGN PATENT DOCUMENTS

JP          10-318933 A    * 12/1998

* cited by examiner

Primary Examiner—Thanh X. Luu
(74) Attorney, Agent, or Firm—F. Chau & Associates, LLC

(57) ABSTRACT

Disclosed is a multi-functioned wafer aligner comprising a multi-functioned unit performing a wafer centering operation, a wafer flat zone alignment, and a wafer damage detection, and a main processor deciding positions of the wafer centering operation and the wafer flat zone alignment, and discriminating wafer damage, such as wafer breakage and wafer crack, by calculating an accumulated digital signal inputted from the multi-functioned unit.

6 Claims, 9 Drawing Sheets

MULTI-FUNCTIONED WAFER ALIGNER

CROSS-REFERENCE TO RELATED APPLICATIONS

This application claims the benefit under 35 U.S.C. §119 of Korean Patent Application No. 2001-11453, filed on Mar. 6, 2001, the disclosures of which are incorporated by reference herein in their entirety.

BACKGROUND OF THE INVENTION

1. Field of the Invention

The present invention relates to a multi-functioned wafer aligner, and more particularly, to a multi-functioned wafer aligner performing a wafer centering compensation, a wafer flat zone alignment, and a wafer breakage or damage detection.

2. Description of Related Art

Recently, rapid developments in the field of semiconductor devices has produced highly integrated and highly efficient storage devices capable of storing enormous quantities of data for processing in short periods of time. Such semiconductor devices are broadly employed in various fields of the information processing industry, computer industry, telecommunication industry, aerospace industry, among many others.

Fabricating such semiconductor devices necessarily includes processes for manufacturing a pure silicon wafer, fabricating multiple semiconductor chips, packaging the chips, and then testing them.

The process of fabricating multiple chips involves a series of very accurate multiple semiconductor fabrication processes, such as for example, a thin film growing/depositing process, an etching process, an ion implanting process, and so forth. The thin film growing/depositing process produces various kinds of thin films with predetermined characteristics on a wafer, the etching process selectively removes a portion of the thin films, and the ion implanting process injects impurities forcedly to improve a thin film or wafer characteristic.

The above-described semiconductor chip fabrication process simultaneously produces multiple semiconductor chips in a wafer of a predetermined diameter to maximize productivity and to improve yields. To produce multiple semiconductor chips simultaneously in a wafer through multiple fabrication processes, the wafer should be always located on and processed in a fixed position of the corresponding equipment to the corresponding process.

To satisfy such requirements, a portion of the wafer sliced from a cylindrical ingot is cut off and a flat zone for recognizing a position of the wafer is generated on the wafer as a result. It is then necessary to adjust the position of the wafer accurately in aligning the flat zone and center the wafer before the wafer is put into the corresponding semiconductor processing equipment. Equipment designed to perform this alignment are normally called a "wafer aligners."

In a typical wafer aligning process, wafers in a lot unit are loaded into a wafer cassette. A wafer transfer arm unloads a wafer from the wafer cassette and transfers it to a rotation chuck, whereupon the wafer is rotated at a predetermined speed by the rotation chuck. A sensor beside the rotation chuck recognizes any eccentric displacement of the wafer, and the wafer transfer arm adjusts the wafer position to center the wafer and eliminate the eccentricity. After centering the wafer, the rotation chuck is rotated to perform a flat zone alignment to the wafer, wherein a sensor detects the flat zone and halts the rotation of the chuck. The wafer transfer arm transfers the wafer from the rotation chuck back to the wafer cassette. After all the wafers have been centered and aligned, the cassette is transferred into the semiconductor fabricating equipment for the next process.

In some systems, after completion of the centering and a flat zone alignment, the wafer is transferred to the semiconductor device fabricating equipment, wherein it is loaded onto a wafer chuck in the equipment and a process performed to the wafer. After the equipment completes the process, the wafer is unloaded from the wafer chuck of the equipment. However, wafer breakage occurs too frequently in this process.

A wafer may break for various reasons. The main reason is that the wafer gets a small crack or a breakage in the wafer edge during a previous manufacturing step. In this case, when stress is overly focused on the crack or the breakage in the wafer edge, the wafer can fatally break during subsequent processing steps, rendering the wafer useless.

Therefore, to prevent such an eventual breakage of the wafer, there is needed a means to inspect and detect the crack or the breakage in the wafer edge before transferring the wafer to the next semiconductor device fabricating step.

SUMMARY OF THE INVENTION

To overcome the above described problems, preferred embodiments of the present invention provide a semiconductor equipment for detecting a crack or damage of a wafer before a semiconductor device fabricating process is performed.

Another purpose of the present invention is to detect a crack or damage of a wafer while either a wafer centering or a wafer flat zone alignment process is performed.

Another purpose of the present invention is clarified by the following detail descriptions.

Disclosed is a multi-functioned wafer aligner comprising a multi-functioned unit performing a wafer centering operation, a wafer flat zone alignment, and a wafer damage detection, and a main processor deciding positions of the wafer centering operation and the wafer flat zone alignment, and discriminating wafer damage, such as wafer breakage and wafer crack, by calculating an accumulated digital signal inputted from the multi-functioned unit.

In another aspect of the invention, the multi-functioned unit comprises a wafer rotator, an array of multiple luminous emitters for emitting incident rays, an array of multiple photo detecting sensors for receiving reflected rays from the wafer to detect a wafer position and a wafer flat zone, wherein each photo detecting sensor faces to each luminous emitter, and an array of multiple damage-detecting sensors for receiving reflected rays from edge of the wafer to detect wafer damage.

In another aspect of the invention, a first area in the array of multiple damage-detecting sensors receives reflected rays when the wafer is not damaged, and a second area in the array of multiple damage-detecting sensors receives reflected rays when the wafer is damaged.

In another aspect of the invention, the main processor further comprises an alarm unit when the second area receives reflected rays.

In another aspect of the invention, the multi-functioned unit comprises an array of multiple luminous emitters for emitting incident rays to the edge of the front side of the wafer and an array of multiple luminous emitters for emitting incident rays to the edge of the back side of the wafer.

In another aspect of the invention, a first area in the array of multiple damage-detecting sensors receives reflected rays when the wafer is not damaged, and a second area in the array of multiple damage-detecting sensors receives reflected rays when the wafer is damaged.

Disclosed is a multi-functioned wafer aligner comprising a rotatable rotation chuck, adapted to receive a semiconductor wafer, a wafer transfer unit, adapted to position said wafer upon said rotation chuck, a sensor body, said sensor body comprising a position compensator, and a wafer damage detector, and wherein said sensor body is disposed in relation to said rotation chuck so as to receive an edge of said wafer within said position compensator.

In another aspect of the invention, said position compensator further comprises a luminous source disposed on a first side of said edge of said wafer, and a photodetector disposed upon an opposing side of said edge of said wafer, said photodetector adapted to receive light emitted by said luminous source.

In another aspect of the invention, said wafer damage detector further comprises a luminous source disposed on a first side of said wafer edge, and a damage-detecting array of sensors adapted to receive light emitted from said luminous source that is reflected off of said wafer edge.

Disclosed is a method of multifunctionally positioning a wafer and detecting wafer damage, said method comprising providing a luminous source on a first side of an edge of said wafer, providing a photodetector on an opposing side of said wafer, said photodetector adapted to receive light emitted by said luminous source, providing a damage-detecting array of sensors adapted to receive light emitted from said luminous source that is reflected off of said wafer edge, rotating said wafer, determining the position of said wafer by examination of light received by said photodetector, inspecting for damage to said wafer by examining the light received by said damage-detecting array of sensors.

BRIEF DESCRIPTION OF THE DRAWINGS

For a more complete understanding of the present invention and the advantages thereof, reference is now made to the following descriptions taken in conjunction with the accompanying drawings, in which like reference numerals denote like parts.

DETAILED DESCRIPTION OF PREFFERED EMBODIMENTS

A multi-functioned aligner of the preferred embodiments according to the present invention and thereof a method for detecting a breakage of a wafer are illustrated in the following statements with the accompanying drawings.

Figure 1:
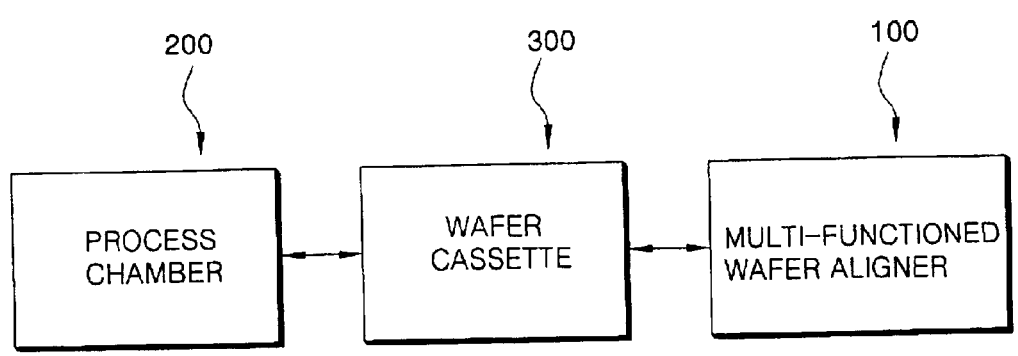
FIG. 1 is a block diagram illustrating a wafer cassette, process equipment, and a multi-functioned wafer aligner according to the preferred embodiment of the present invention.

Referring to FIG. 1, the multi-functioned aligner 100 according to the present invention unloads a wafer from a wafer cassette 300 and performs a wafer centering procedure, a wafer flat zone alignment, and a wafer breakage detection before a next processing equipment 200 executes a semiconductor device fabricating process to the wafer. If the wafer is found to have no damage, such as crack or breakage, in during the breakage detection, the wafer is loaded back to the wafer cassette 300 and finally to the processing equipment 200.

Figure 2:
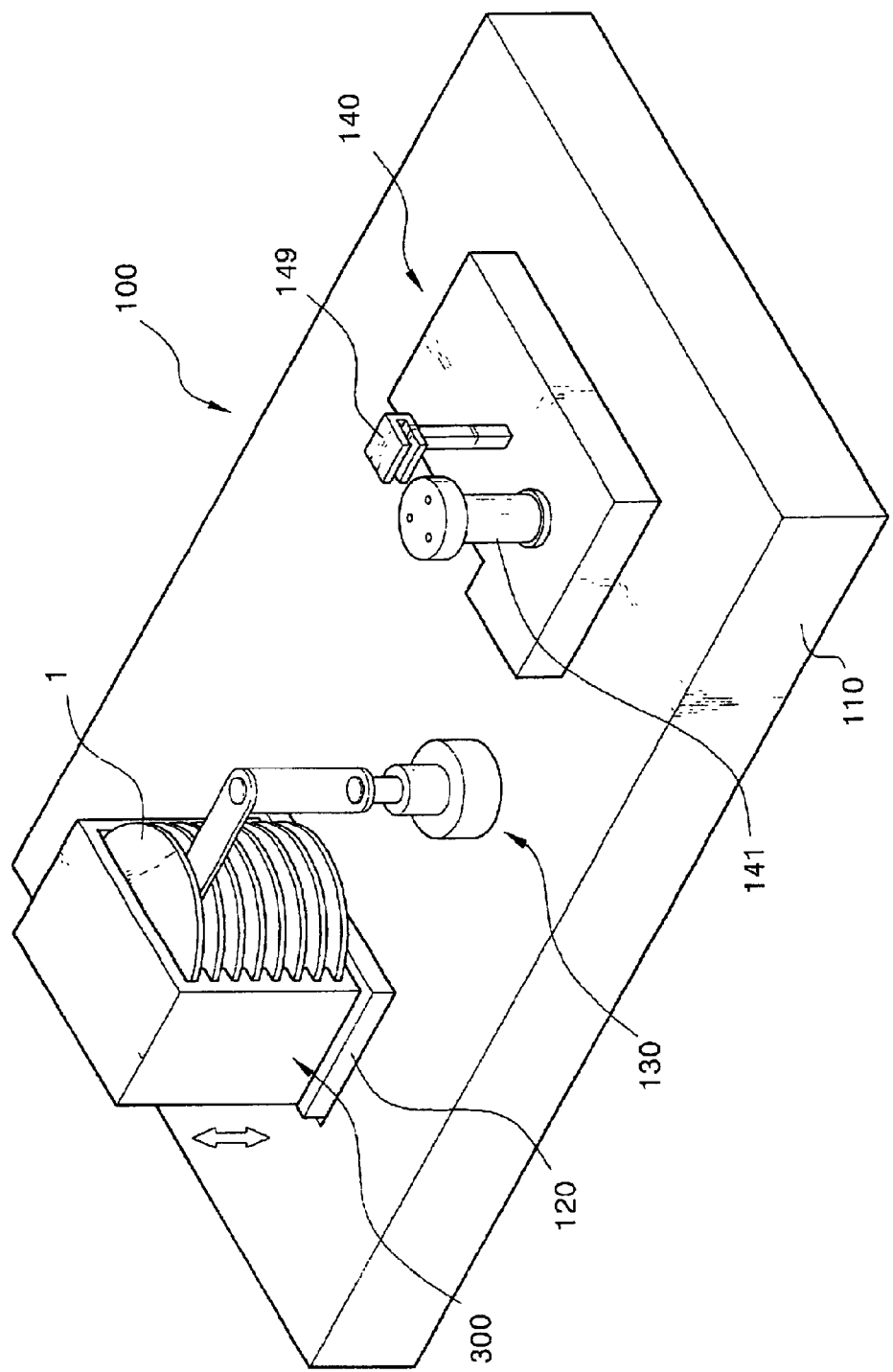
FIG. 2 is a perspective view of the multi-functioned aligner according to the present invention.

FIG. 2 is a perspective view of the multi-functioned aligner 100 according to the present invention so as to illustrate the entire configuration of the multi-functioned aligner 100 performing a wafer centering operation, a wafer flat zone alignment, and a wafer damage detection.

In overview, the multi-functioned aligner 100 according to the present invention comprises a base body 110, a wafer cassette loader 120, a wafer transfer 130, a multi-functioned unit 140 and a main processor.

In detail, the base body 110 having a hexahedron shape installs the wafer cassette loader 120 on the topside of the base body 110. The wafer transfer unit 130 is installed adjacently to the wafer cassette loader 120 and the multi-functioned unit 140 is installed adjacently to the wafer transfer unit 130. The wafer cassette loader 120 moves up and down by a wafer cassette elevator (not shown) to load a wafer from the wafer cassette 300.

On the contrary, the wafer transfer 130 transfers a wafer from the wafer cassette 300 to the multi-functioned unit 140 or vice versa. The multi-functioned unit 140 receiving a wafer from the wafer transfer unit 130 performs a wafer centering operation, a wafer flat zone alignment, and a wafer damage detection.

Figure 3:
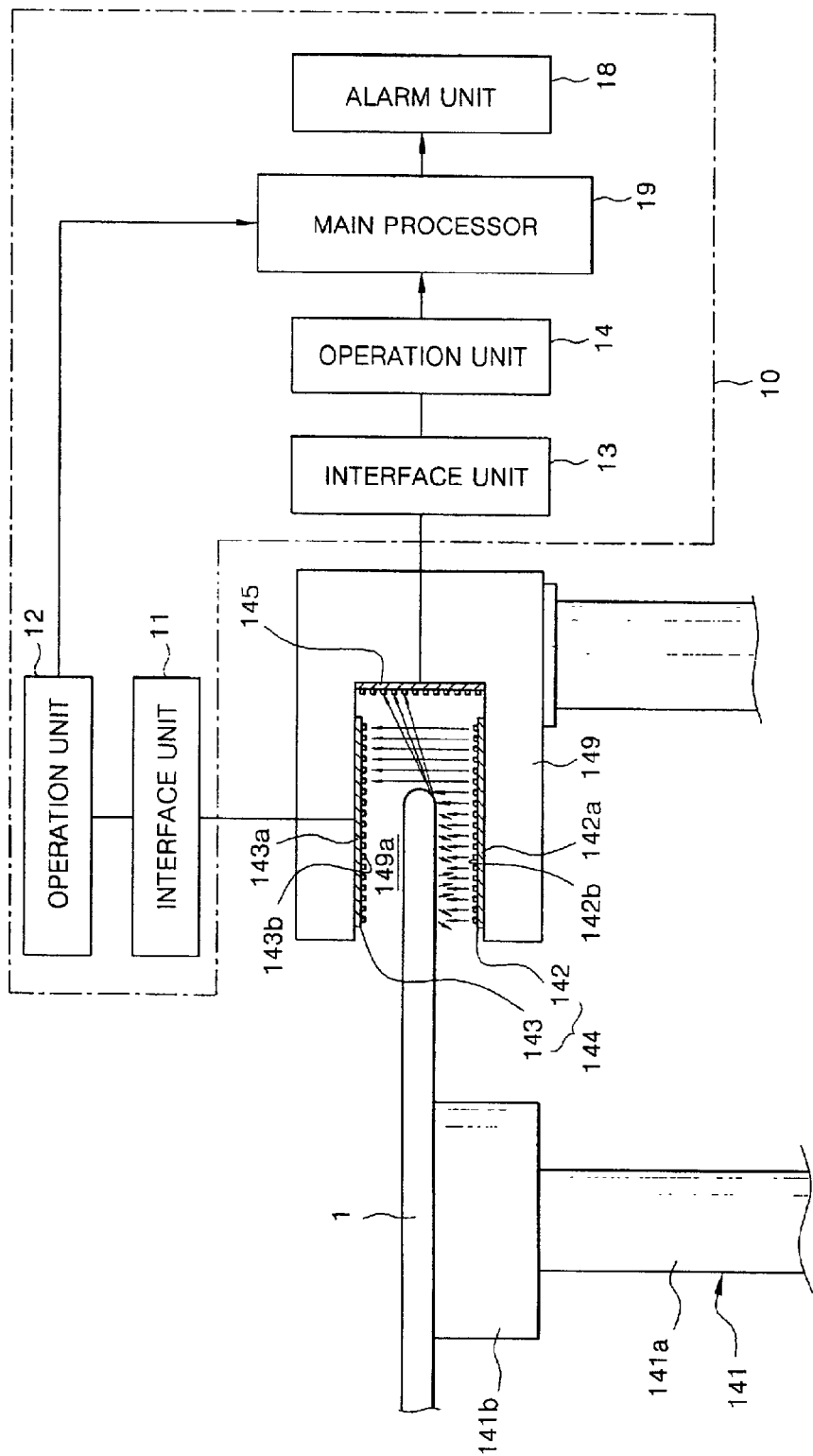
FIG. 3 is a drawing illustrating a configuration of a multi-functioned unit of the multi-functioned aligner according to the present invention.

Referring to FIGS. 2 and 3, the multi-functioned unit 140 comprises a wafer rotator 141, a position compensator 144 for compensating a position of a wafer centering and a wafer flat zone, a wafer damage detector 145, and a sensor body 149, the sensor body comprising the position compensator 144 and the wafer damage detector 145. The position compensator 144 and the wafer damage detector 145 are electrically connected into a main processor 10.

In more detail, the wafer rotator 141 comprises a rotation generator (e.g., a motor, not shown), a rotation axis 141a installed in the rotation generator, and a rotation chuck 141b installed in the end of the rotation axis 141a for rotating a wafer 1 horizontally.

The rotation chuck 141b comprises at least one vacuum hole for holding firmly onto the wafer by vacuum pressure 1 and thereby removing any rotation slip between the wafer 1 and the rotation chuck 141b when the rotation chuck 141b is rotated.

The sensor body 149 is positioned so that the edge of the wafer 1 is inserted into the sensor body 149 when the wafer 1 is loaded from the side of the rotation chuck 141b to the topside of the rotation chuck 141b.

In detail, the sensor body 149 comprises a block shape including a wafer insertion groove 149a having a predetermined depth into the side of the block. The wafer insertion groove 149a has a sufficient interval so that the edge of the wafer 1 can be easily positioned within the sensor body 149. The sensor body 149 is connected to the base body 110 by a connecting rod.

The position compensator 144 is installed in both the top and the bottom side of the wafer insertion groove 149a of the sensor body 149. The position compensator 144 comprises a luminous source 142 and a photodetector 143. In detail, the luminous source 142 comprises a luminous plate 142a and a plurality of luminous emitters 142b installed in a high density matrix on the topside of the luminous plate 142a in the arrangement of a luminous emitter array.

The number of the luminous emitters 142b is proportional to the desired accuracy of a wafer centering operation and a wafer flat zone alignment. A light source going straight with less spreading and diffracting characteristics can be employed in the luminous emitter 142b.

The photodetector 143, opposite the luminous source 142, comprises a photo detecting plate 143a and photo detecting sensors 143b installed in a high density matrix on the topside of the photo detecting plate 143a. The photo detecting sensors 143b collectively are referred to as the photo detecting sensor array.

Each luminous emitter 142b corresponds to a photo detecting sensor 143b.

When a photo detecting sensor 143b receives the ray emitted from the corresponding luminous emitter 142b, the photo detecting sensor 143b generates a predetermined magnitude of a current flow to be inputted into a main processor 19 through an interface unit 11 and a calculation unit 12 in a type of a digital signal.

The digital signal inputted into the main processor 19 includes the position of the photo detecting sensor 143b within the photo detecting sensor array. In other words, the main processor 19 can identify the precise photo detecting sensor 143b receiving the ray emitted from the luminous emitter 142b.

Figure 4:
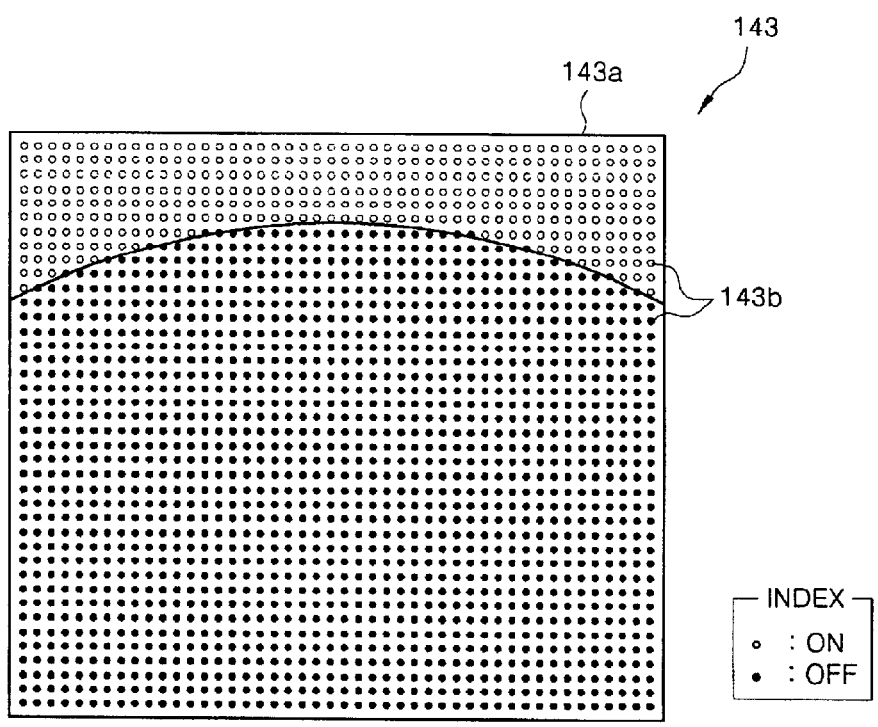
FIGS. 4 and 5 are drawings illustrating on/off states of a photodetector when the multi-functioned aligner performs a wafer centering process according to the present invention.

FIG. 4 is a drawing illustrating on/off states of a photodetector when the multi-functioned aligner performs a wafer centering process according to the present invention. Black dots and white dots are positions of the photo detecting sensor 143b. The black dots are interpreted as the areas not to receive any rays. In other words, the main processor 19 recognizes the areas that the wafer 1 interrupts the rays from the luminous sources 142. The main processor 19 recognizes the areas of the white dots that the wafer 1 does not interrupt the rays from the luminous sources 142. By the digital signal inputted into the main processor 19, the main processor 19 can decide whether the wafer centering operation is correct or not. The following illustrates such an example.

Figure 5:
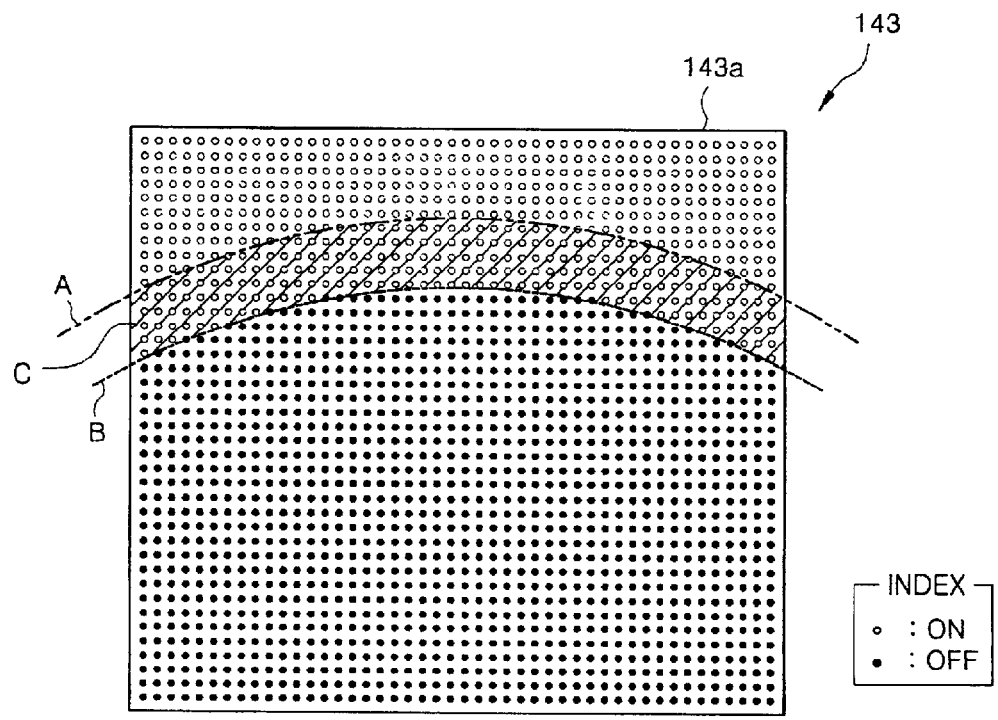

In this example, the areas of the black dots in FIG. 4 are assumed in the case that the wafer centering operation is correct. Referring to FIG. 5, the areas below the boundary A should be dotted in black, when the wafer centering operation is correct. It is evident in comparison with the areas in FIG. 4.

However, the areas below the boundary B are actually dotted in black in FIG. 5. Offset areas C between the boundary A and the boundary B mean that the wafer centering operation is not correct in such an amount of the offset areas.

According to on/off states of the photo detecting sensor 143b in the photo detecting sensor array, position data for the wafer 1 on the rotation chuck 141b is accumulated at least more than once. By utilizing the accumulated position data, the main processor 19 calculates the wafer centering data needed to center the wafer 1.

Sequentially, the main processor 19 orders the wafer transfer 130 to adjust the centering position. As a result, the wafer transfer unit 130 transfers the wafer 1 on the rotation chuck 141b back and forth, or left and right, according to the wafer centering data inputted from the main processor 19. While adjusting the wafer centering position on the rotation chuck 141b, wafer damage is also detected.

Figure 6:
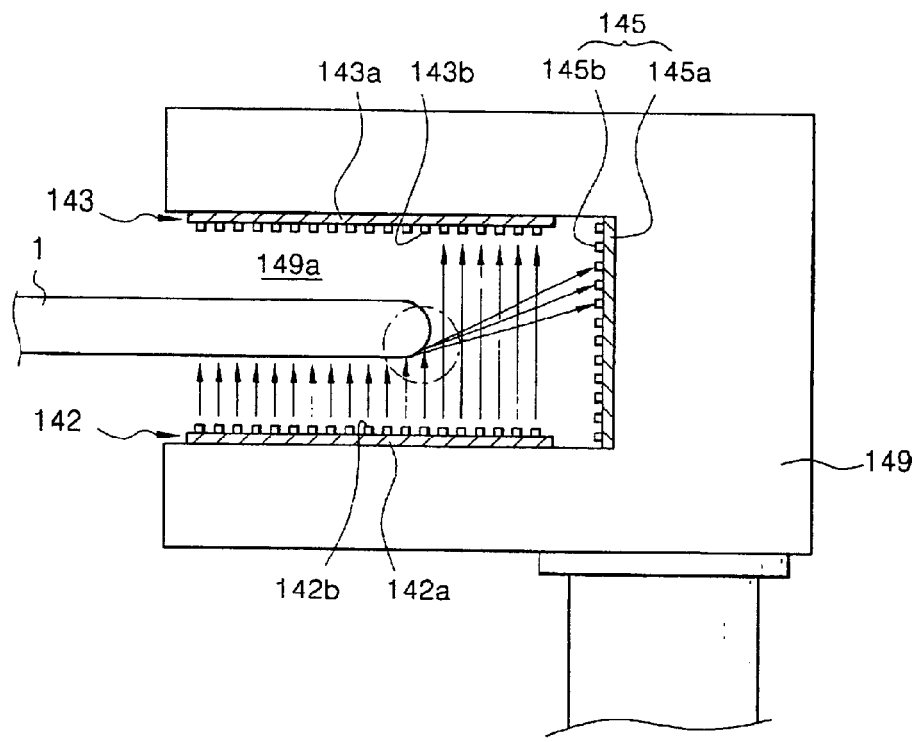
FIG. 6 is a cross-sectional view illustrating a luminous source and a photodetector of a multi-functioned unit in the absence of wafer damage.

Referring to FIG. 6, the wafer damage detector 145 is installed in the sensor body 149 to detect wafer damage. In detail, the wafer damage detector 145 is installed in the wafer insertion groove 149a of the sensor body 149. The wafer damage detector 145 is positioned substantially perpendicularly to the luminous source 142 of the position compensator 144.

The wafer damage detector 145 comprises a damage detecting plate 145a and a damage-detecting sensor array comprising a high density matrix of damage-detecting sensors 145b mounted on the topside of the damage detecting plate 145a.

The output signal from the damage-detecting sensors 145b of the damage-detecting sensor array is calculated in the interface unit 13 and the calculation unit 14 shown in FIG. 3, and finally inputted into the main processor 19. The wafer damage detector 145 only detects damage of the wafer 1.

Figure 7:
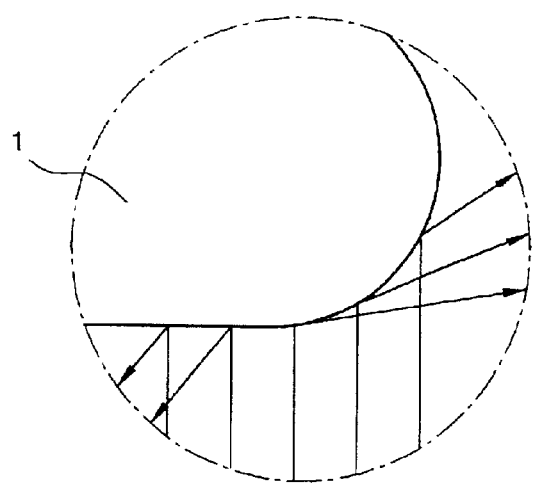
FIG. 7 is a magnification view of an edge of the wafer reflecting incident rays according to FIG. 6.
Figure 8:
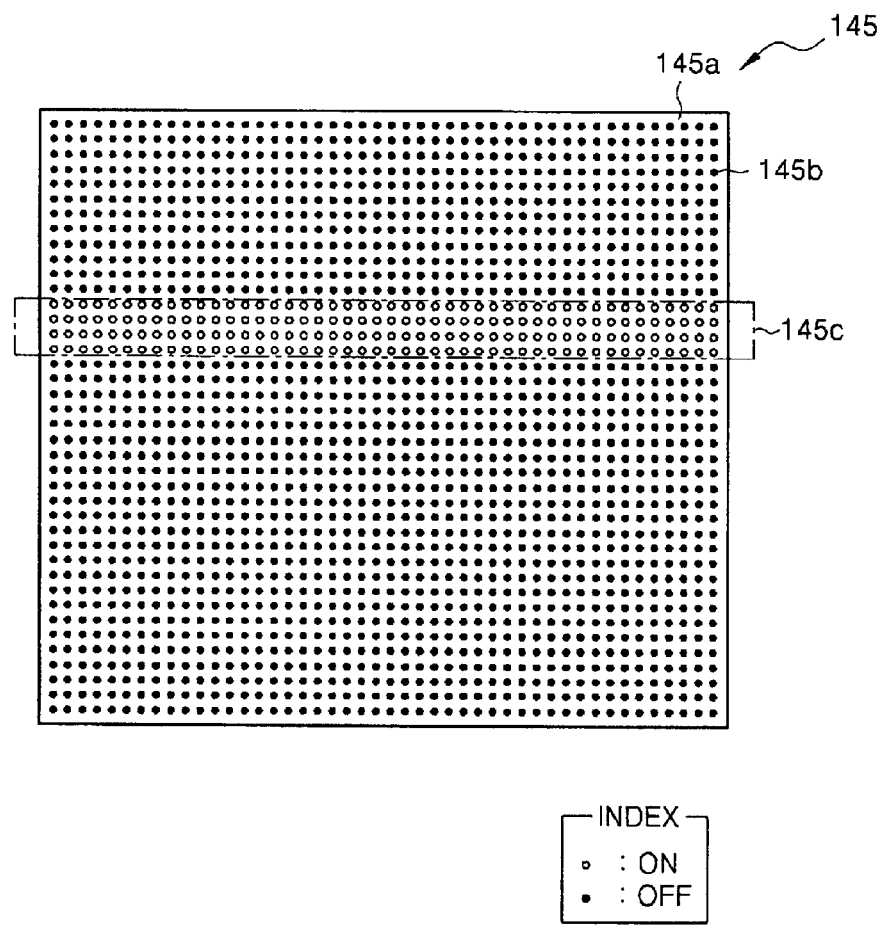
FIG. 8 is a drawing illustrating on/off states of a photodetector according to FIG. 6.

FIGS. 6, 7 and 8 illustrate the operation of the damage detector 145 in the presence of an undamaged wafer 1.

Generally, the edge of the wafer 1 is rounded (edge rounding) to prevent a stress force concentration of an external impact. When the wafer 1 is not damaged as shown in FIG. 7, the rounded edge of the wafer 1 evenly and consistently reflects the incident rays from the luminous emitter 142b of the position compensator 144, to a tangential direction off the edge of the wafer (total reflection) and radially away from the center of the wafer. In this case, the reflected rays in the edge of the wafer 1 intensively arrive at assigned positions of the damage-detecting sensor 145b of the damage-detecting sensor array, for example, a first area 145c in the wafer damage detector 145 as shown in FIG. 8.

Figure 9:
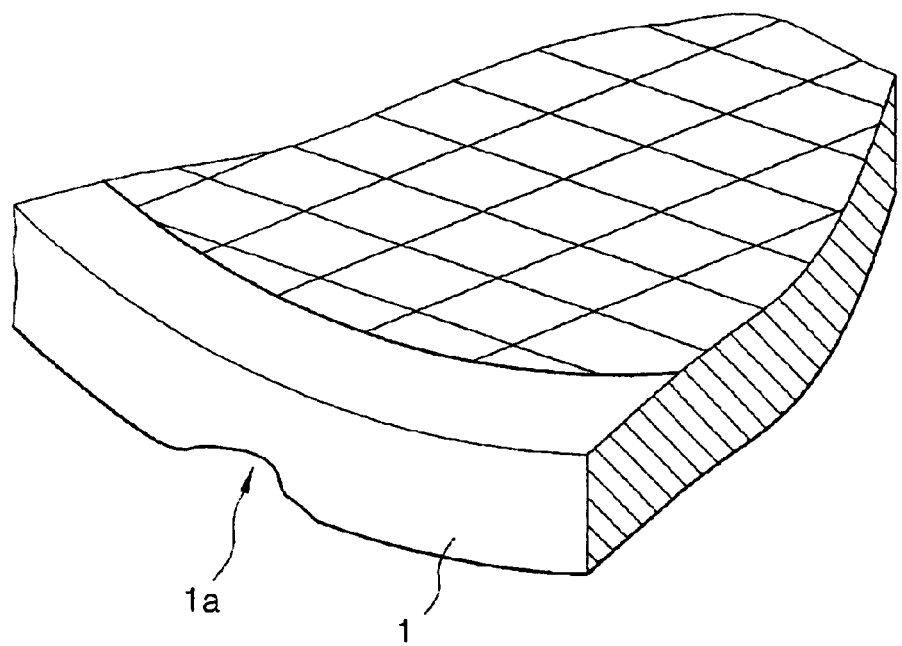
FIG. 9 is a sectional perspective view illustrating a breakage of a wafer.
Figure 10:
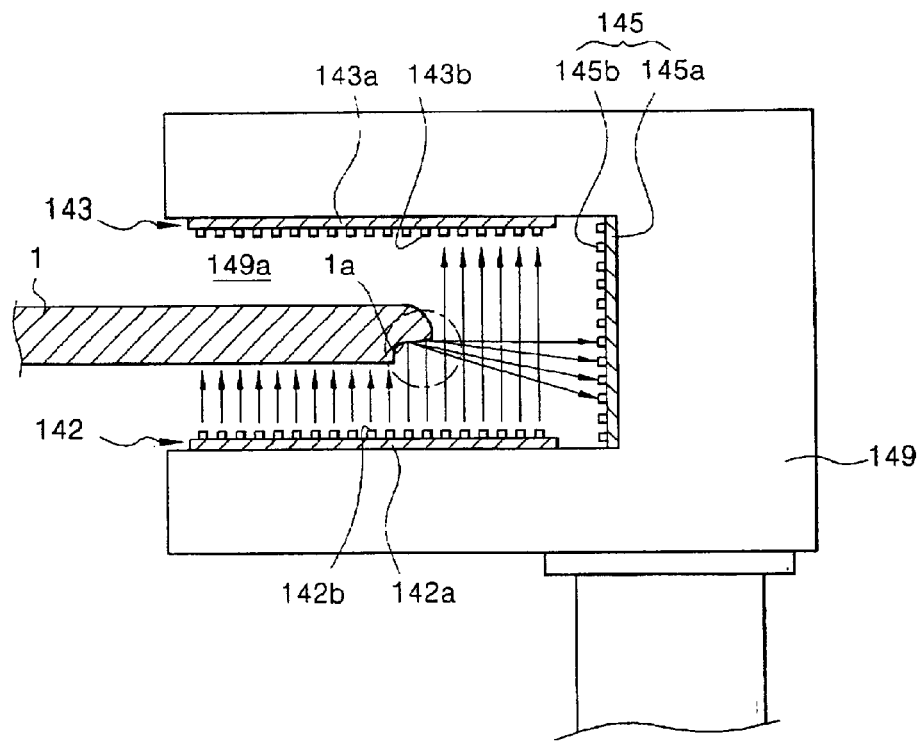
FIG. 10 is a drawing illustrating a luminous source and a photodetector of a multi-functioned unit in the presence of wafer damage, such as crack or breakage.
Figure 11:
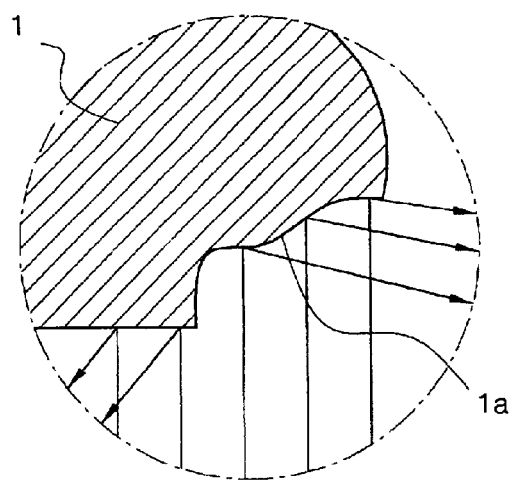
FIG. 11 is a magnification view of an edge of the wafer reflecting incident rays according to FIG. 10.
Figure 12:
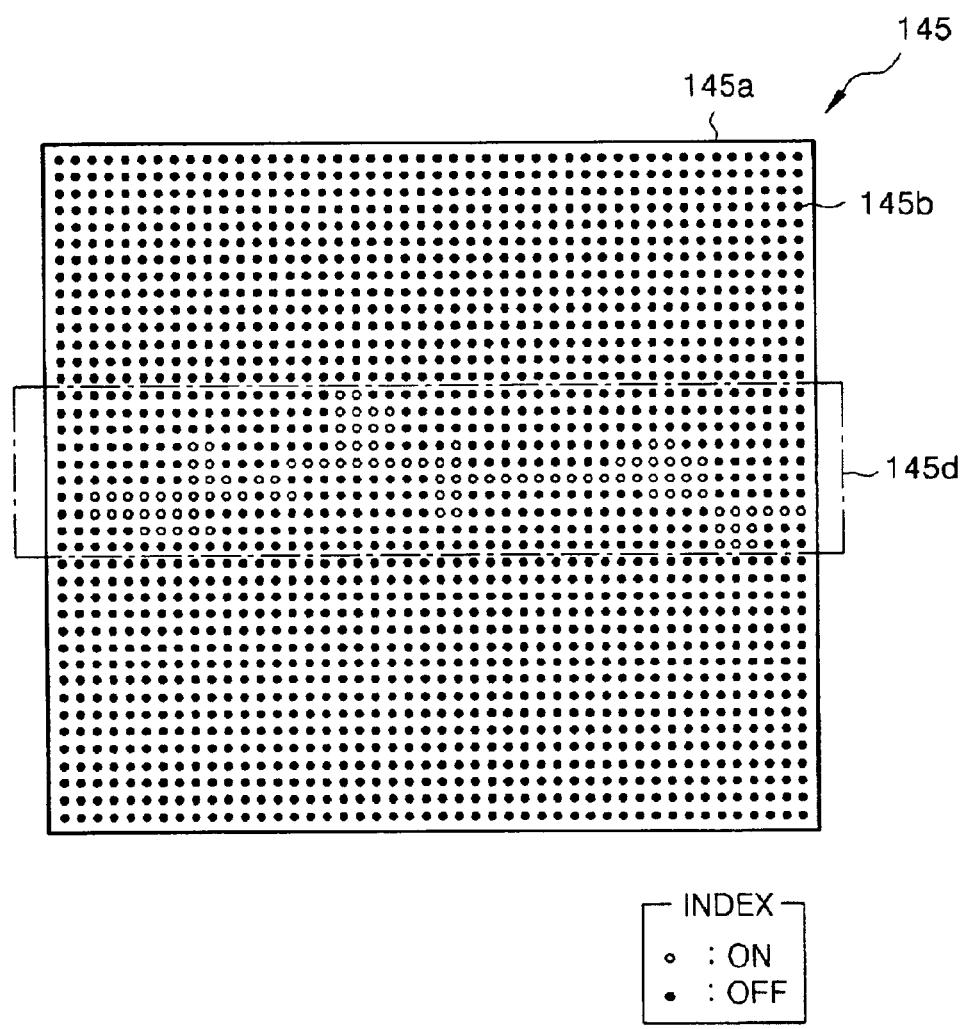
FIG. 12 is a drawing illustrating on/off states of a photodetector according to FIG. 10.

However, when the wafer 1 is damaged about the edges as shown in FIG. 9, the broken or cracked edge of the wafer 1 scatters the incident rays from the luminous emitter 142b of the position compensator 144 as shown in FIG. 10 and FIG. 11 (scattered reflection). As a result, the reflected rays arrive at unpredictable positions of the damage-detecting sensor 145b, for example, a second area 145d as shown in FIG. 12.

According to the above described illustrations, the positions of the damage-detecting sensors 145b picking up light signals in the presence of wafer damage are different from those in the absence of wafer damage, allowing the main processor 19 to quickly identify the broken wafer.

When the main processor 19 decides that the wafer 1 is broken, an alarm unit 18 is operated until an appropriate action is taken. When the main processor 19 decides that the wafer 1 is not broken, the alignment of the flat zone on the wafer goes ahead as planned.

The flat zone, a cutoff portion of the edge of the wafer 1, has different on/off areas in the photo detecting sensor 143b from the other portion of the wafer 1. Therefore, the main processor can stop the rotation chuck 141b when the flat zone is accurately aligned beneath the photodetector array. As a result, the flat zone alignment of the wafer 1 is completed.

After flat zone alignment, the wafer is unloaded from the rotation chuck 141b by the wafer transfer unit 130 and is again unloaded to the wafer cassette 300. Finally, the wafer cassette 300 is transferred to the next manufacturing process equipment 200 where the next semiconductor device fabrication process is performed.

As illustrated in the above detail descriptions, wafer damage, such as breakage or crack, can be quickly identified during the wafer centering operation and the defective wafer discarded before further costly and time-consuming manufacturing steps are wasted upon it. The larger the diameter of the wafer is, the more effective to the wafer breakage the present invention is.

The preferred embodiment of the present invention employs a single multi-function unit to detect wafer damage, such as breakage or crack, especially in the bottom of the edge of the wafer, though of course a separate damage detector and alignment detector could be used. By using a single unit, however, both space and resources are saved because the light emitted by the luminous source does double duty.

An additional multi-functioned unit may be employed to detect wafer damage on the upper surface of the wafer edges. The second unit would simply be mounted upside down. The second unit would not need a photodetector 143, but a photodetector may be included regardless for purposes of redundancy or for improved accuracy.

While the invention has been particularly shown and described with reference to preferred embodiments thereof, it will be understood by those skilled in the art that the foregoing and other changes in form and details may be made therein without departing from the spirit and scope of the invention.

What is claimed is:

1. A method for positioning a wafer and detecting wafer damage, the method comprising:

inserting a peripheral region of a wafer to a sensor body;

emitting rays from an array of luminous emitters on a first surface of the sensor body:

receiving emitted rays by a first array of photo detecting sensors on a second surface of the sensor body opposite the first surface;

determining a position of the wafer based on the emitted rays received by the first array of photo detecting sensors;

receiving emitted rays, which are reflected by the wafer, by a second array of photo detecting sensors on a third surface of the sensor body orthogonal to the first surface and the second surface of the sensor body; and determining wafer damage based on the emitted rays received by the second array of photo detecting sensors.

2. A multi-functioned wafer aligner comprising:

a multi-functioned unit for performing wafer centering, wafer flat zone alignment, and wafer damage detection;

the multi-functioned unit comprising:

a wafer rotator;

a sensor body comprising;

an array of luminous emitters disposed on a first surface of the sensor body for emitting incident rays;

an array of photo detecting sensors disposed on a second surface of the sensor body opposite the first surface for receiving the incident rays emitted by the array of luminous emitters; and an array of damage-detecting sensors disposed on a third surface of the sensor body for receiving the incident rays that are reflected from edges of a wafer to detect wafer damage; and a processor for determining positions of the wafer for performing the wafer centering and the wafer flat zone alignment based on light received by the array of photo detecting sensors, and determining wafer damage based on light received by the array of damage detecting sensors.

3. The multi-functioned wafer aligner of claim 2, wherein the array of photo detecting sensors receive no incident ray when the wafer interrupts the incident rays from the array of luminous emitters.

4. The multi-functioned wafer aligner of claim 2, wherein a first area in the array of damage-detecting sensors receives reflected rays when the wafer is not damaged, and a second area in the array of damage-detecting sensors receives reflected rays when the wafer is damaged.

5. The multi-functioned wafer aligner of claim 4, wherein the processor further comprises an alarm unit when the second area receives reflected rays.

6. A multi-functioned wafer aligner comprising:

a rotatable chuck, adapted to receive a semiconductor wafer;

a wafer transfer unit, adapted to position said wafer upon said rotatable chuck;

a sensor body, comprising:

an array of luminous emitters disposed on a first surface of the sensor body for emitting incident rays;

an array of photo detecting sensors disposed on a second surface of the sensor body opposite the first surface for receiving the incident rays emitted by the array of luminous emitters; and an array of damage-detecting sensors disposed on a third surface of the sensor body orthogonal to the first surface and the second surface for receiving said rays that is reflected off of an edge of said wafer wherein said sensor body is disposed in relation to said rotatable chuck so as to receive an edge of said wafer.

* * * * *